US008165266B2

(12) United States Patent
Wear et al.

(10) Patent No.: US 8,165,266 B2
(45) Date of Patent: Apr. 24, 2012

(54) TRANSVERSE SCANNING BONE DENSITOMETER AND DETECTOR USED IN SAME

(75) Inventors: James Wear, Madison, WI (US); David Ergun, Verona, WI (US); Robert Washenko, Madison, WI (US); Michael Bucholz, Oregon, WI (US); Darrell Gorsuch, Pardeeville, WI (US); Randall Payne, Madison, WI (US)

(73) Assignee: General Electric Company, Niskayuna, NY (US)

( * ) Notice: Subject to any disclaimer, the term of this patent is extended or adjusted under 35 U.S.C. 154(b) by 95 days.

(21) Appl. No.: 12/557,314

(22) Filed: Sep. 10, 2009

(65) Prior Publication Data

US 2011/0058649 A1  Mar. 10, 2011

(51) Int. Cl.
*G01N 23/06* (2006.01)
(52) U.S. Cl. ................... 378/55; 378/98.8; 250/370.13
(58) Field of Classification Search ................ 378/55, 378/98.8, 54; 250/370.08, 370.09, 370.13
See application file for complete search history.

(56) References Cited

U.S. PATENT DOCUMENTS

| 4,255,659 | A | 3/1981 | Kaufman et al. | 378/146 |
|---|---|---|---|---|
| 4,794,257 | A | 12/1988 | Baba et al. | 250/370.09 |
| 5,177,776 | A * | 1/1993 | Ohmori et al. | 378/98.2 |
| 5,306,306 | A * | 4/1994 | Bisek et al. | 600/407 |
| 6,081,582 | A | 6/2000 | Mazess et al. | 257/442 |
| 6,928,144 | B2 * | 8/2005 | Li et al. | 378/98.8 |
| 6,975,012 | B2 | 12/2005 | Moriyama et al. | 250/370.01 |
| 7,196,332 | B2 | 3/2007 | Wear et al. | 250/370.01 |

* cited by examiner

*Primary Examiner* — Courtney Thomas
(74) *Attorney, Agent, or Firm* — Fletcher Yoder, P.C.

(57) ABSTRACT

A scanning bone densitometer includes an x-ray source to produce x-rays and an x-ray detector receiving x-rays emitted from the x-ray source. The x-ray detector includes a cadmium telluride (CdTe) semiconductor. The scanning bone densitometer also includes a controller moving the x-ray source and the x-ray detector along a transverse scanning path to acquire a plurality of scan images of an object of interest.

20 Claims, 5 Drawing Sheets

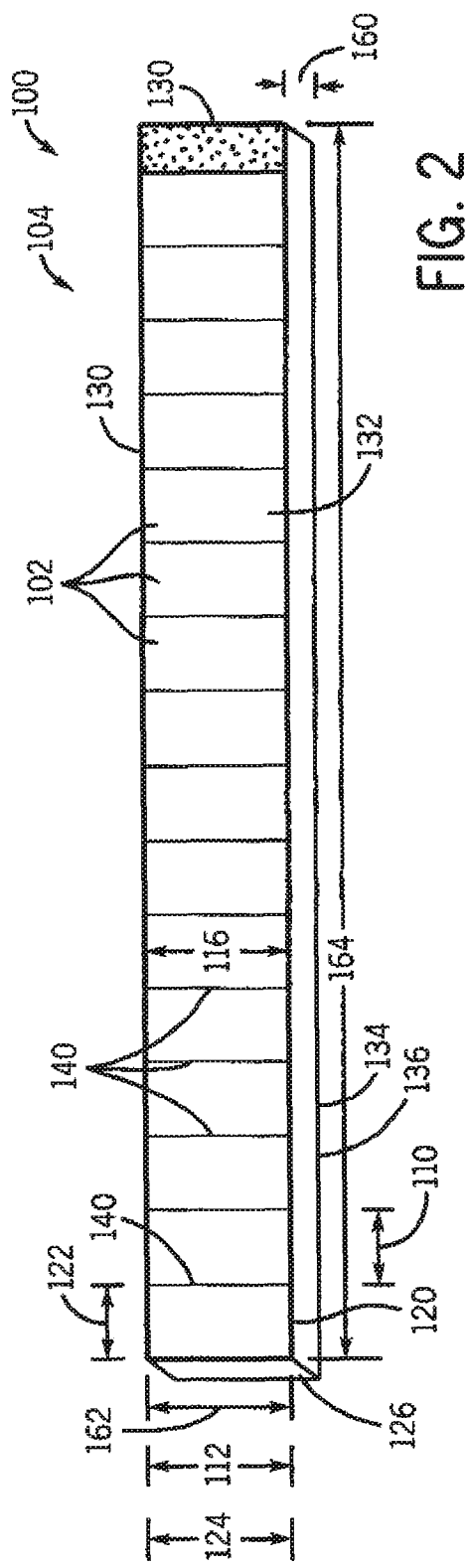
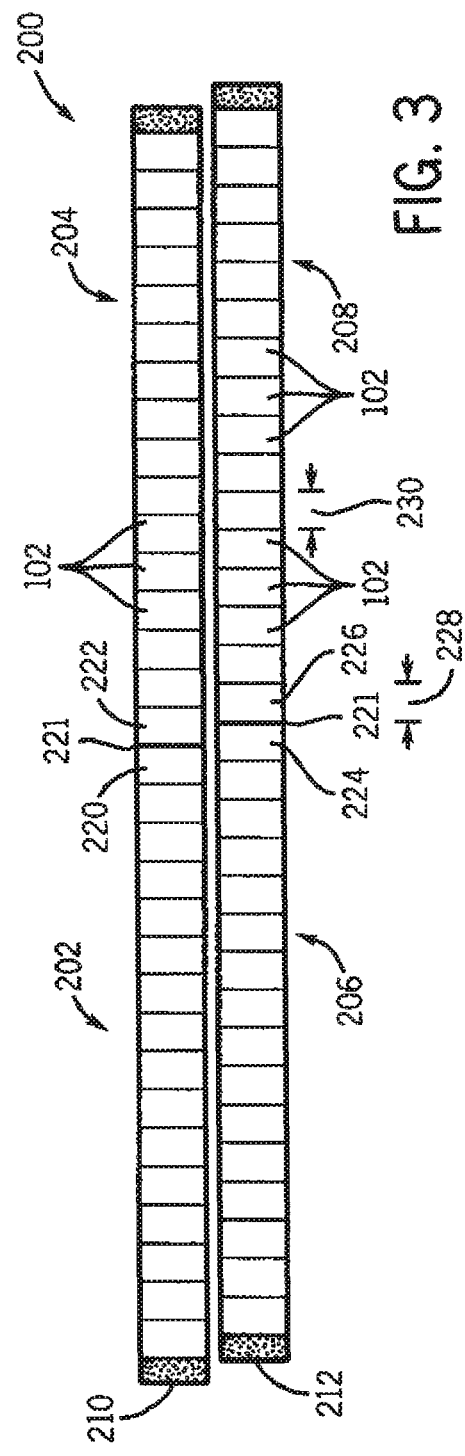

TRANSVERSE SCANNING BONE DENSITOMETER AND DETECTOR USED IN SAME

BACKGROUND OF THE INVENTION

The subject matter disclosed herein relates generally to medical diagnostic imaging systems, and more particularly to bone densitometers.

Dual-energy imaging systems include an x-ray source that emits a collimated beam of dual-energy x-rays to image a patient. An x-ray detector is positioned with respect to the x-ray source to receive the x-rays passing through the patient. The x-ray detector produces electrical signals in response to the received x-rays. The electrical signals are converted to digital signals that are utilized by the imaging system to generate images of the patient.

Measurements of the x-ray absorption by an object at two different x-ray energies can reveal information about the composition of that object as decomposed into two selected basis materials. In the medical area, the selected basis materials are frequently bone and soft tissue. The ability to distinguish bone from surrounding soft tissue allows x-ray images to yield quantitative information about in vivo bone density for the diagnosis of osteoporosis and other bone disease.

At least some known dual-energy imaging systems include detector elements that are fabricated using a Cadmium Telluride (CdTe) semiconductor having conventional ohmic anode and cathode contacts. Under the influence of an applied biasing voltage, the semiconductor generates a current proportional to the energy of each x-ray absorbed by the semiconductor. The slight increases in the semiconductor current due to x-rays are translated into digital signals that are used to generate an image. However, the conventional ohmic contacts may generate substantial leakage current that causes noise and thus reduces the overall quality of the signal used to generate the images.

BRIEF DESCRIPTION OF THE INVENTION

In accordance with one embodiment, a scanning bone densitometer is provided. The densitometer includes an x-ray source to produce x-rays and an x-ray detector receiving x-rays emitted from the x-ray source. The x-ray detector includes a cadmium tellurium (CdTe) semiconductor. The densitometer also includes a controller moving the x-ray source and the x-ray detector along a transverse scanning path to acquire a plurality of scan images of an object of interest.

In accordance with another embodiment, an x-ray detector is provided. The x-ray detector includes a cathode, an anode, and a plurality of cadmium tellurium (CdTe) semiconductors disposed between the cathode and the anode. The CdTe semiconductors are configured to convert x-rays emitted from a dual-energy transverse scanning x-ray source into a charge that is proportional to the x-ray energy.

In accordance with a further embodiment, a method of fabricating a dual-energy system x-ray detector is provided. The method includes depositing an platinum cathode on a first surface of a cadmium tellurium (CdTe) semiconductor that is configured to convert x-rays emitted from a dual-energy transverse scanning x-ray source into a charge that is proportional to the x-ray energy, and depositing an indium Schottky contact on an opposite surface of the CdTe.

BRIEF DESCRIPTION OF THE DRAWINGS

FIG. 2 is an illustration of an exemplary detector that may be used with the imaging system shown in FIG. 1 in accordance with various embodiments.

FIG. 3 is an illustration of another exemplary detector that may be used with the imaging system shown in FIG. 1 in accordance with various embodiments.

DETAILED DESCRIPTION OF THE INVENTION

Figure 1:
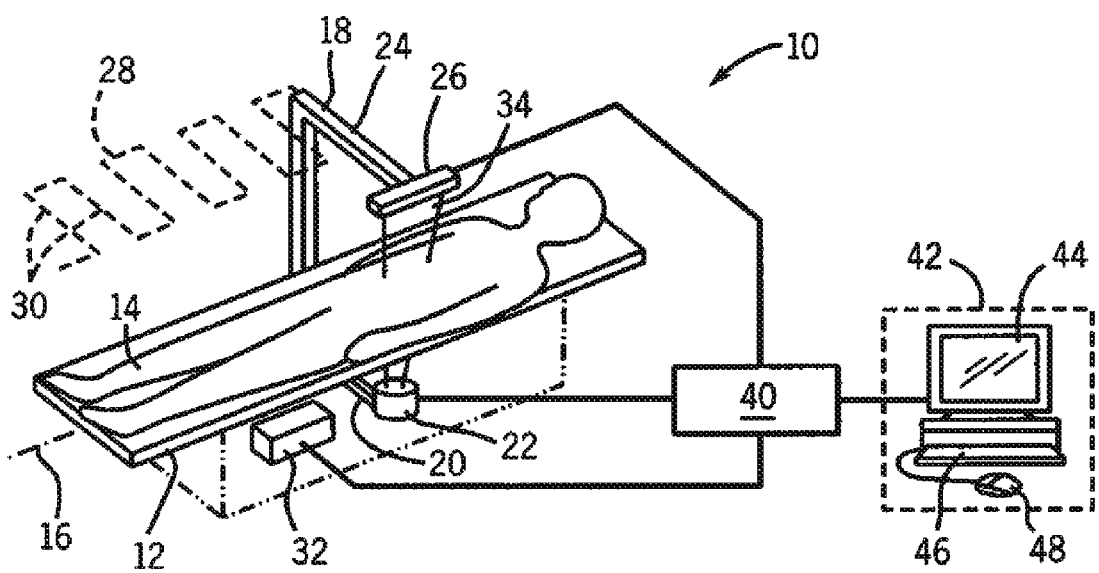
FIG. 1 is a block diagram of a dual-energy x-ray imaging system formed in accordance with various embodiments illustrating a full body scan.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. One or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Exemplary embodiments of dual-energy x-ray systems and methods for acquiring, for example bone and tissue information are described in detail below. In particular, a detailed description of an exemplary dual-energy x-ray system will first be provided followed by a detailed description of various embodiments of methods and systems for acquiring and measuring bone mineral density, bone tissue information, and other bone related information that may be used to diagnose a medical condition such as osteoporosis for example.

At least one technical effect of the various embodiments of the systems and methods described herein is to acquire accurate bone density information using a dual-energy x-ray imaging system. In some embodiments, a single dual-energy x-ray scan, and more particularly, a single body scan is used to acquire image information for a number of different bones, from which bone lengths are determined.

FIG. 1 is a block diagram of an exemplary dual-energy x-ray system, illustrated as a dual x-ray absorptiometry (DEXA or DXA) system 10, which is also referred to as dual energy bone densitometer system capable of performing bone densitometry. The system 10 constructed in accordance with various embodiments is configured to measure at least an area of a bone, a length of a bone, a bone mineral content (BMC), a bone mineral density (BMD), and a tissue thickness or density. The BMD is calculated by dividing the BMC by the area of the bone. During operation, an x-ray beam with broadband energy levels is utilized to scan an object, for example, to scan a human subject to image the bones of the human subject. The acquired images of the bones are used to diagnose a medical condition such as osteoporosis. The images may be generated in part from determined bone density information acquired during a dual-energy x-ray scan.

The system 10 includes a patient table 12 providing a horizontal surface for supporting a subject, for example, a patient 14 in a supine or lateral position along a longitudinal axis 16. The system 10 also includes a support member, for example, a C-arm 18. The C-arm 18 has a lower end 20 that is positioned beneath the patient table 12 to support an x-ray source 22. The C-arm 18 has an upper end 24 that is positioned above the patient table 12 supporting an x-ray detector 26. Optionally, the x-ray detector may be coupled to the lower end 20 and the x-ray source 22 coupled to the upper end 24. The x-ray detector 26 may be fabricated, for example, as a multi-element cadmium-tellurium (CdTe) detector providing for energy discrimination. The x-ray source 22 and the x-ray detector 26 may be moved in a raster pattern 28 so as to trace a series of transverse scans 30 of the patient 14 during which dual energy x-ray data is collected by the x-ray detector 26. The transverse scanning procedure generates either a single image or quantitative data set, from a plurality of scan images acquired across a patient, wherein the x-ray source 22 and the detector 26 are either longitudinally aligned with the superior-inferior axis of the patient or transversely from the patient's left to right. Scanning a patient using a transverse motion facilitates minimizing the time between acquisitions of adjacent scan images because the transverse direction across the patient is shorter than the longitudinal direction across the patient. Thus transverse scanning can reduce the severity of patient motion artifacts between scan images allowing the images to be more accurately merged.

The transverse scanning motion is produced by actuators (not shown) under control of a translation controller 32. During operation, the x-ray source 22 produces a fan beam 34 having a plane that is parallel to the longitudinal axis 16. Optionally, the fan beam 34 may have a plane that is perpendicular to the longitudinal axis 16. The raster pattern 28 is adjusted such that there is some overlap (e.g., slight overlap of 10 percent) between successive scan lines of the fan beam 34. The x-ray source 22, the x-ray detector 26, and the translation controller 32 communicate with, and are under the control of, a computer 40 which may include both dedicated circuitry and one or more processors having the ability to execute a stored program.

Referring again to FIG. 1, the computer 40 communicates with a terminal 42 including a display 44, a keyboard 46, and a cursor control device such as a mouse 48 allowing for operator input and the output of text and images to the operator. In some embodiments, the computer 40 is located remotely from the workstation 42. Optionally, the computer 40 may form a portion of the workstation 42. The computer is adapted to perform one or more processing operations. The acquired bone and tissue information, for example, image and density information may be processed and displayed in real-time during a scanning session as the data is received. Additionally or alternatively, the data may be stored temporarily in a memory device on the computer 40 during a scanning session and then processed and displayed in an off-line operation. The information may also be stored in a long-term storage device (e.g., hard-drive or server) for later access, such as during a follow-up scan of the same patient and useful to monitor, for example, the change in bone and tissue density over a period of time. The display 44 includes one or more monitors that present patient information, including the scanned image and the bone length images to the operator for diagnosis and analysis. The displayed images may be modified and the display settings of the display 44 also manually adjusted using the keyboard 46, the mouse 48, or a touch screen icon on the display itself.

During operation, the system 10 is configured to operate in either a dual energy x-ray mode or a single energy x-ray mode. In the single energy mode, the x-ray source 22 emits x-rays at a narrow band of energies of a few keV and in the diagnostic imaging range of approximately 20-150 keV. In the dual-energy mode, the x-ray source 22 emits radiation at two or more bands of energy emitted simultaneously or in rapid succession. The x-ray source 22 may also be configured to emit a single broadband energy of more than a few keV over the diagnostic imaging range. The system 10 may be switched between the dual energy mode and the single energy mode by increasing or decreasing the x-ray source 22 voltage and/or current. The system may also be switched between the dual energy mode and the single energy mode by removing or adding a K-edge filter. It should be noted that the x-ray source 22 may emit x-rays at different energies or ranges of energies.

The x-ray source 22 may be configured to output a fan beam of x-rays 34 as shown in FIG. 1. The x-ray source 22 may also be configured to output a pencil beam of x-rays (not shown), a cone beam of x-rays, or other configurations. In some embodiments, the computer 40 controls the system 10 to operate in the single energy mode or dual-energy mode to determine the bone or tissue information of at least some of the scanned body. The single energy mode generally enables higher resolution images to be generated. The acquired images may then be used to measure, for example, bone density or other bone and tissue characteristics or content. As discussed above, the dual-energy x-ray scan may be a rectilinear scan of the entire patient body, which may be performed in a transverse-type scanning sequence as described above. During the dual-energy x-ray scan an image of the entire body of the patient may be acquired, which includes image information relating to the bones and tissue in the body. The full body or total body scan of the entire body may be performed as a single scanning operation, which may be a low dose mode scan. In some embodiments, instead of a full body or total body scan, individual rectangular regions of the body may be performed, which may be single sweep scans. Once the scan of the patient, or a portion thereof, is completed, the dual energy signals provided by the detector 26 are deconstructed into images of two basis materials, such as bone and soft tissue. The high and low energy signals can also be combined to provide a single energy mode having superior signal to noise ratio for imaging purposes.

The detector 26 shown in FIG. 1 may be embodied as either a linear array of detector elements, a side linear array of detector elements, which includes two transversely separated rows of detector elements, or a stacked array detector in which the detector elements are stacked along a direction of propagation of the radiation and are selectively sensitive to low and high energy spectrums, respectively.

FIG. 2 is an illustration of an exemplary detector 100 including a plurality of detector elements 102 arranged as a linear array that may be used with the imaging system 10 shown in FIG. 1. In one embodiment, the plurality of detector elements 102 are formed as a monolithic structure on a single ceramic substrate. Optionally, the plurality of detector elements 102 are fabricated individually and then assembled together to form the detector 100. In the exemplary embodiment, the detector 100 includes a plurality of detector elements 102, illustrated as sixteen cadmium tellurium (CdTe) detector elements 102 that are oriented to form the linear array 104. Utilizing CdTe detector elements 102 enhances the image quality of images by enabling the detector 100 to produce images using a photon counting technique. For example, during a hip scan, if a full intensity x-ray beam passes from a high attenuating hip region to air, the detector elements 102 reduce or eliminate space-charge polarization that can cause a subsequent region of a scan to have no counts or erroneous counts. The exemplary detector 100, using CdTe detector elements 102 has improved hole transport properties, for example compared to CZT detector elements. Therefore, the CdTe detector elements have improved immunity to space charge polarization when exposed to x-rays, which is desirable when scanning patients using the imaging system 10 described herein.

Referring again to FIG. 2, in the exemplary embodiment, at least some of the detector elements 102 have a width 110 that is approximately 1.5 millimeters and a length 112 that is approximately 2.7 millimeters. It should be appreciated that the width 110 and the length 112 of the detector elements 102 is exemplary and that other widths and lengths may be selected based on the imaging application. In the exemplary embodiment, the detector 100 also includes at least one other detector element 120 having a width 122 that is approximately 1.4 millimeters and a length 124 that is approximately 2.7 millimeters.

As shown in FIG. 2, the detector element 120 is disposed at an end 126 of the detector array 104. The plurality of detector elements 102 and 120 are configured into sixteen sensing electrodes having a guard ring 130, that functions as a ground, surrounding the detector elements 102 and 120 on a cathode side 132. The detector 100 also includes a single anode electrode 134 that is formed on a side 136 that is opposite to the cathode side 132. In the exemplary embodiment, the detector elements 102 and 120 are each separated by a non-conductive gap 140 such that the detector elements 102 and 120 have an approximately 1.60 mm electrode pitch. In the exemplary embodiment, the gap 140 is filled with a non-metallized material. In the exemplary embodiment, the detector 100 has a thickness 160 that is between approximately 0.1 millimeters and 3.0 millimeters to enable sufficiently high x-ray absorption efficiency to ensure the scan is dose efficient. Moreover, in the exemplary embodiment, the detector has a width 162 and a length 164 and a thickness 160, wherein the width 162 is approximately 3.0 millimeters and the length 164 is approximately 26.0 millimeters and the thickness 160 is approximately 1.0 millimeters.

FIG. 3 is an illustration of another exemplary detector 200 including a plurality of detector elements 102 arranged as a staggered array that may be used with the imaging system 10 shown in FIG. 1. In the exemplary embodiment, the detector 200 includes four monolithic detectors 202, 204, 206, and 208 that form the detector 200. In the exemplary embodiment, each of the four monolithic detectors 202, 204, 206, and 208 are coupled together to form the detector 200. Optionally, the detector 200 may be fabricated such that the four monolithic detectors 202, 204, 206, and 208 are formed as a unitary structure. Specifically, the detector 200 may be fabricated as a single unit to include the four monolithic detectors 202, 204, 206, and 208. In the exemplary embodiment, each detector 202, 204, 206, and 208 is a single monolith that is substantially similar to the monolithic detector 100 shown in FIG. 2.

The detector 200 is arranged in a 2×2 array that includes two columns 210 and 212 wherein each column includes two monolithic detectors. The column 210 includes the detectors 202 and 204 and the column 212 includes the detectors 206 and 208. In the exemplary embodiment, each detector 202, 204, 206, and 208 includes sixteen detector elements 102. Each column 210 and 212 therefore includes 32 detector elements 102 which are offset by a distance that is approximately ½ the width of a single detector element, e.g. approximately 0.8 millimeters. As such, in the exemplary embodiment, the detector 200 includes sixty-four total detector elements 102. In one embodiment the four detectors 202, 204, 206, and 208 used to form the detector 200 are formed on a single ceramic substrate. Optionally, the four detectors 202, 204, 206, and 208 used to form the detector 200 are fabricated individually and then assembled together to form the detector 200. In the exemplary embodiment, each detector 202, 204, 206, and 208 includes sixteen cadmium tellurium (CdTe) detector elements 102 that are oriented to form the linear staggered detector array 200. As shown in FIG. 3, each detector 202, 204, 206, and 208 includes a respective undersized detector element 220, 222, 224, and 226 that are similar to the detector element 120 shown in FIG. 2. The undersized detector elements 220, 222, 224, and 226 each have a width 228 that is less than a width 230 of the other detector elements. The width of the detector elements 220, 222, 224, and 226 is reduced to maintain the electrode pitch across the gap between the detector elements as discussed above.

The detectors 202, 204, 206, and 208 are arranged such that the detector element 220 is adjacent to the detector element 222 and the detector element 224 is adjacent to the detector element 226. Moreover, the gap 221 is defined between the detector elements 220 and 222 the detector elements 224 and 226. In the exemplary embodiment, the gap 221 is an air gap. The staggered detector arrangement shown in FIG. 3 improves the longitudinal image sampling without resorting to smaller pixels.

Optionally, the detector 200 may be a stacked array detector in which the detector elements 102 are stacked along the direction of propagation of the radiation and are selectively sensitive to low and high energy spectrums, respectively. A particular advantage of the stacked array detector is that the stacked array detector can easily accommodate a multi-linear array or area detector design. Each of the detectors described herein includes a plurality of independent detector elements that are arranged along at least one line to provide a scan image of having a width that may be extended by extending the width of the detector. For example, the width of the scan may be increased by adding additional detector sections to the detector 200. Once the scan is complete, the dual energy signals provided by the detector are deconstructed into images of two basis materials, such as bone or soft tissue. The high and low energy signals can also be combined to provide a single energy mode having superior signal to noise ratio for imaging purposes.

Figure 4:
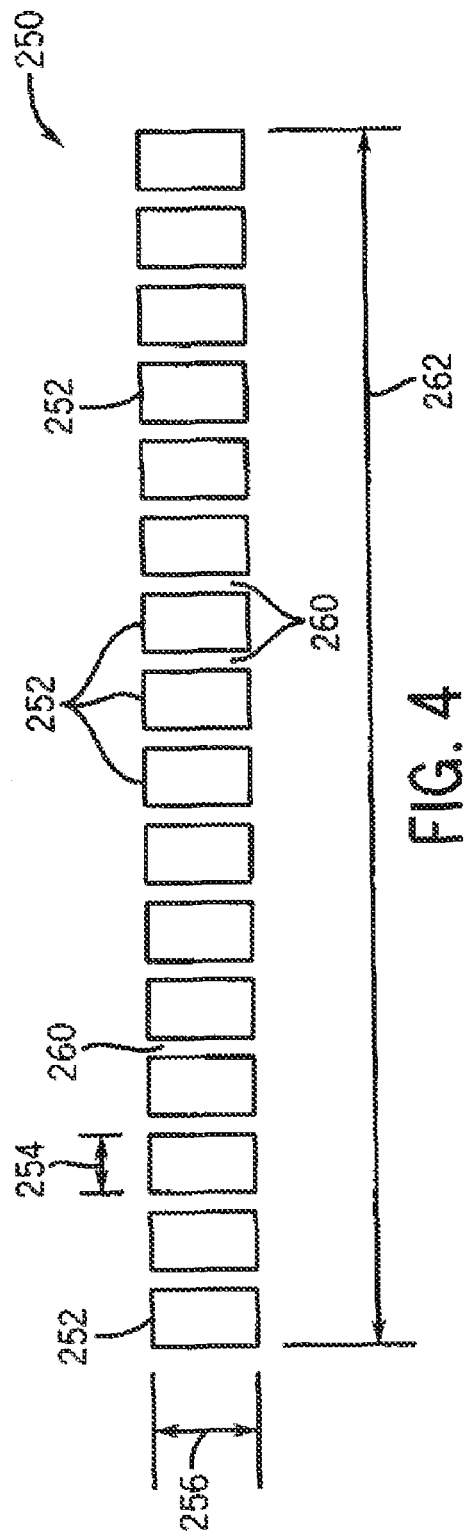
FIG. 4 is an illustration of another exemplary detector that may be used with the imaging system shown in FIG. 1 in accordance with various embodiments.

FIG. 4 is an illustration of another exemplary detector 250 including a plurality of detector elements 252 arranged as a linear array that may be used with the imaging system 10 shown in FIG. 1. In the exemplary embodiment, the plurality of detector elements 252 are discrete detector elements 252 that are fabricated individually and then assembled together to form the detector 250. In the exemplary embodiment, the detector 250 includes a plurality of detector elements 252, illustrated as sixteen cadmium tellurium (CdTe) detector elements 252 that are oriented to form the linear array.

In the exemplary embodiment, the detector elements 252 have a width 254 that is approximately 3.0 millimeters and a length 256 that is approximately 7.0 millimeters. It should be appreciated that the width 254 and the length 256 of the detector elements 252 is exemplary and that other widths and lengths may be selected based on the imaging application. In the exemplary embodiment, the detector elements 252 are each separated by a non-conductive or air gap 260 such that the detector 250 has an overall length 262 of approximately 51.0 millimeters. Each detector element 252 includes a single anode and a single cathode that is formed on a side that is opposite to the anode. In the exemplary embodiment, the detector 250 has a thickness of approximately 0.75 millimeters.

Figure 5:
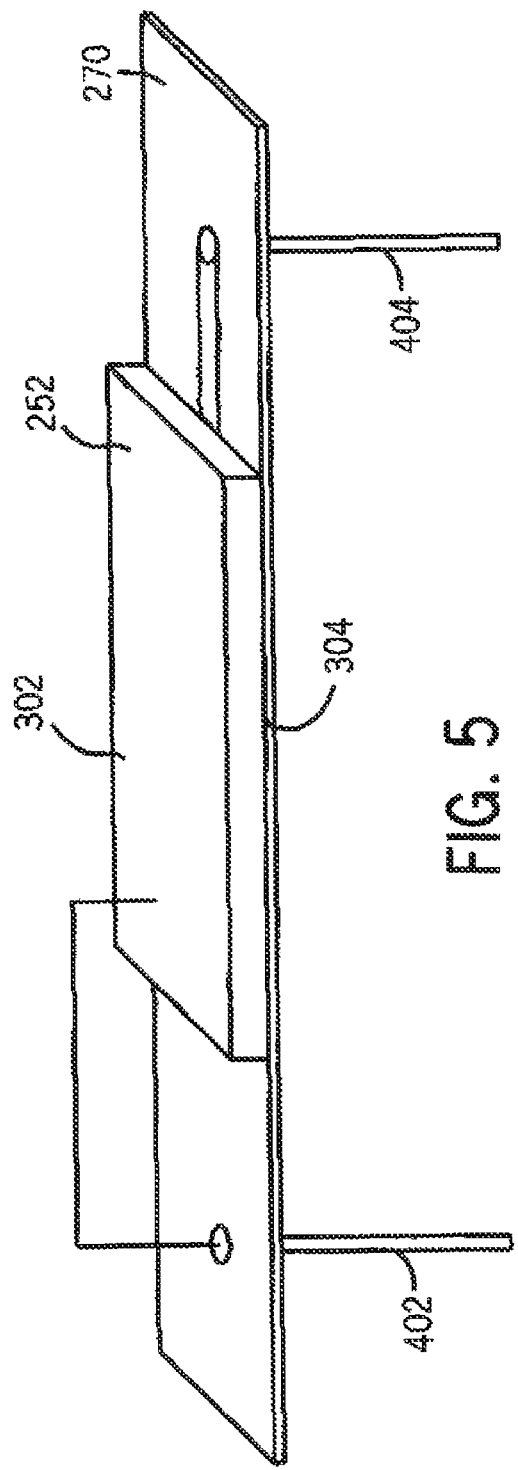
FIG. 5 is a top perspective view of the detector shown in FIG. 4 formed on a substrate in accordance with various embodiments.

FIG. 5 is a top perspective view of a single detector element 252 shown in FIG. 4 formed on a substrate 270 in accordance with various embodiments. In the exemplary embodiment, each detector element 252 includes a cathode 302 and an anode 304. During assembly, the cathode 302 is electrically coupled to a common cathode 402. The detector element anode 304 is electrically coupled to a common anode 404. The single detector cathode 402 and the single detector anode 404 enable electrical outputs from the detector to be transmitted to the imaging system for further processing. For example, the electrical outputs from the cathode 402 and the anode 404 may be transmitted to a computer, e.g. the computer 40 shown in FIG. 1. The computer 40 then may utilize various algorithms to reconstruct an image of the subject using the information received from the cathode 402 and the anode 404.

Figure 6:
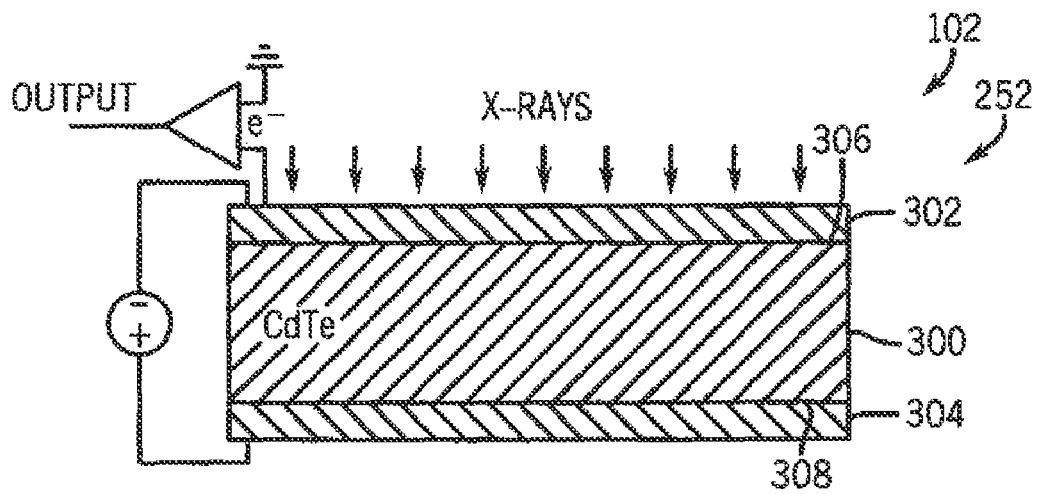
FIG. 6 is a side view of an exemplary detector element that may be used with the detectors shown in FIGS. 2-5 in accordance with various embodiments.

FIG. 6 is a side view of an exemplary detector element 102 that can be used with any of the detectors described herein. In the exemplary embodiment, the detector element 252 is substantially similar to detector element 102. Therefore, it should be realized that the following description of detector element 102 is also applicable to detector element 252. As shown in FIG. 6, the detector element 102 includes a CdTe semiconductor crystal 300. The detector element 102 also includes a cathode 302 and an opposing anode 304. The cathode 302 is disposed on an x-ray impinging surface 306, e.g. the surface of the detector element 102 on which the x-rays impinge. The anode 304 is disposed on an opposing surface 308 of the semiconductor crystal 300. The cathode 302 and the anode 304 may be disposed on the wafer 300 using a chemical vapor deposition technique, sputtering and/or metal plating for example. In the exemplary embodiment, the cathode 302 is fabricated using a platinum material and the anode 304 is fabricated using at least one of an indium material or an aluminum material. The combination of the wafer 300, the cathode 302, and the anode 304 form a diode. In the exemplary embodiment, the anode 304 is fabricated from the indium or aluminum material to form a Schottky contact or blocking contact/element when a positive bias is applied between the anode 304 and the cathode 302. For example, at least some known detector elements are fabricated using a Cadmium Telluride (CdTe) semiconductor having conventional ohmic anode and cathode contacts. Under the influence of an applied biasing voltage, the semiconductor generates a current proportional to the energy of each x-ray absorbed by the semiconductor. The slight increases in the semiconductor current due to x-rays are translated into digital signals that are used to generate an image. However, the conventional ohmic contacts may generate substantial leakage current that causes noise and thus reduces the overall quality of the signal used to generate the images. Whereas, the detector elements 102 described herein each include an anode 304 that forms a Schottky contact that greatly reduces semiconductor leakage currents, thereby reducing noise and enabling accurate estimation of each x-ray's energy.

During operation, each detector element 102 produces an electric charge that is caused by the ionization of x-rays incident on the detecting surface of the detector element 102. The signal is produced using an electric bias that is applied between the cathode 302 and the anode 304 as shown in FIG. 6. The combination of the CdTe semiconductor 300 and the indium anode 304 enables the detector element 102 to function as a Schottky contact. The Schottky contact substantially blocks leakage current, thus enabling the detector element 102 to measure the energy of each x-ray and classify the x-ray's energy as either a low-energy x-ray or a high-energy x-ray. During operation, the detector element 102 simultaneously measures the low-energy and high-energy content of a single broadband x-ray energy beam.

Figure 7:
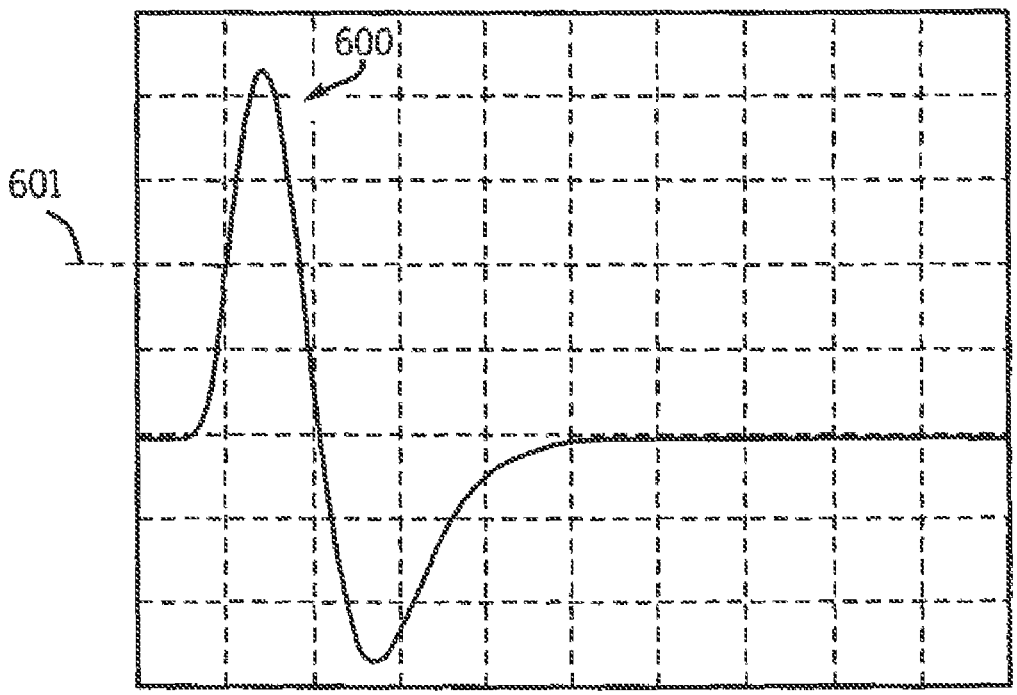
FIG. 7 is a graphical illustration of an exemplary output received from a single exemplary detector element in accordance with various embodiments.

For example, FIG. 7 is a graphical illustration of an exemplary output received from a single exemplary detector element 102 wherein the x-axis represents the x-ray energy and the y-axis represents the quantity of x-rays measured at a given x-ray energy. The output from the detector element 102 is an electrical pulse that is generated in response to x-rays impinging on the detector element 102 wherein the amplitude of the pulse is proportional to the energy of the absorbed x-ray. As shown in FIG. 7, if the x-ray energy of the single pulse 600 exceeds a predetermined threshold 601 than the pulse 600 is classified as a high-energy pulse. Whereas, if the single pulse is below the threshold 601 the pulse 600 is classified as a low-energy pulse. For example, if the single pulse 600 is equal to or less than 40 keV than the pulse 600 is classified as a low-energy pulse. In the exemplary embodiment, the broadband x-ray source emits x-rays having an energy of approximately 40 keV which are classified as low-energy x-rays, and x-rays having an energy of approximately 80 keV which are classified as high-energy x-rays.

Figure 8:
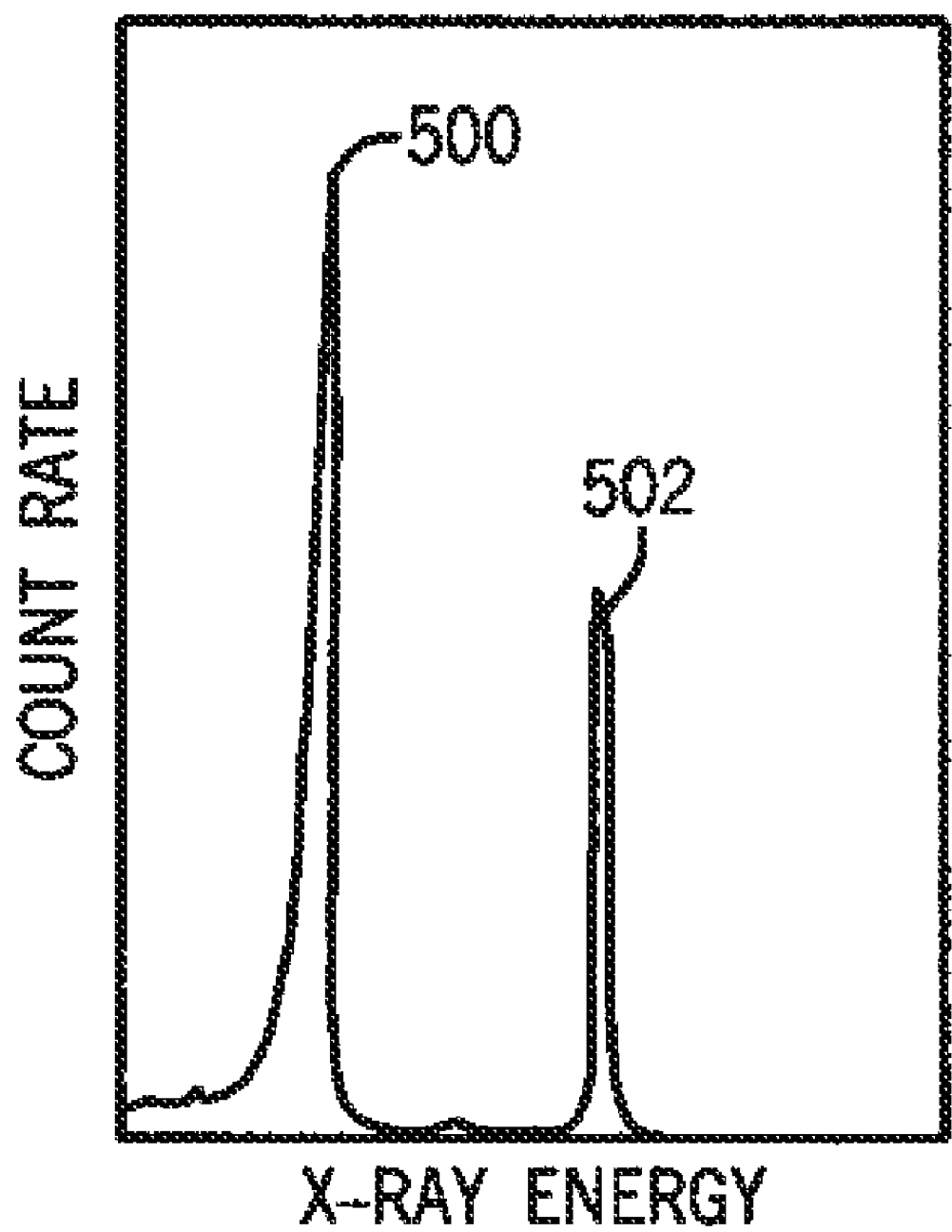
FIG. 8 is a graphical illustration of an exemplary output from the detector shown in FIGS. 2, 3, and 4 in accordance with various embodiments.

FIG. 8 is a graphical illustration of an exemplary output from the detector shown in FIGS. 2, 3, and 4 in accordance with various embodiments wherein the x-axis represents the detector element 102 (or detector channel) and the y-axis represents the count rate. As discussed the x-ray pulses are classified as either low-energy or high-energy. As shown in FIG. 8, the cumulative count rate 500 for x-rays absorbed at a first x-ray energy is greater than a count rate 502 of x-rays absorbed at a second lower energy. In the exemplary embodiment, the Schottky contact 304 enables the detector elements 102 to discriminate between x-rays received at various energy levels and transform the received x-rays into counts.

The detector element 102, including the Schottky contact 304 is capable of withstanding the higher voltage levels that may be used with the dual-energy imaging system without being affected by a corresponding increasing in leakage current. Moreover, the CdTe detector element 102 has a lower cost than conventional CZT detector elements providing significant cost savings particularly with the monolith array device.

A method of fabricating a dual-energy system x-ray detector includes depositing an platinum cathode on a first surface of a cadmium tellurium (CdTe) semiconductor that is configured to configured to convert x-ray beams emitted from a dual-energy transverse scanning x-ray source into a current that is proportional to the x-ray beams, and depositing an indium Schottky contact on an opposite surface of the CdTe. The method further includes arranging a plurality of CdTe semiconductors to form at least one of a linear detector array and a staggered detector array.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A scanning bone densitometer comprising:
an x-ray source configured to produce x-rays;
an x-ray detector configured to receive x-rays emitted from the x-ray source, the x-ray detector including a cadmium tellurium (CdTe) semiconductor detector element, wherein the CdTe semiconductor detector element comprises an anode and a cathode, the anode comprising at least one of an indium material or an aluminum material and the cathode comprising a platinum material; and
a controller configured to move the x-ray source and the x-ray detector along a transverse scanning path to acquire a plurality of scan images of an object of interest, wherein the transverse scanning path comprises a first path transverse to a longitudinal axis of the object of interest, a second path parallel to the longitudinal axis of the object of interest, and the transverse scanning path repeatedly alternates between the first and second paths.

2. The scanning bone densitometer of claim 1 wherein the x-ray source comprises a dual-energy x-ray source.

3. The scanning bone densitometer of claim 1 wherein the x-ray detector comprises a plurality of CdTe semiconductor detector elements, each CdTe semiconductor detector element comprising a photon-counting element.

4. The scanning bone densitometer of claim 1 wherein the x-ray detector comprises a plurality of CdTe semiconductor detector elements, each CdTe semiconductor detector element comprising a Schottky contact.

5. The scanning bone densitometer of claim 1 wherein the x-ray detector comprises a plurality of CdTe semiconductor detector elements.

6. The scanning bone densitometer of claim 1 wherein the x-ray detector comprises a plurality of linear CdTe semiconductor detector arrays arranged in a staggered arrangement.

7. The scanning bone densitometer of claim 1 wherein the x-ray detector comprises a plurality of CdTe semiconductor detector elements arranged to form a linear detector array.

8. The scanning bone densitometer of claim 1 wherein the x-ray detector comprises a plurality of CdTe semiconductor detector elements, each CdTe semiconductor detector element being separated from an adjacent CdTe semiconductor detector element by a gap.

9. The scanning bone densitometer of claim 1 wherein the x-ray detector comprises sixteen CdTe semiconductor detector elements, each CdTe semiconductor detector element comprising a current blocking contact.

10. The scanning bone densitometer of claim 1 further comprising a computer programmed to:
acquire information from a dual-energy x-ray scan of a subject; and
generate a dual-energy image of the subject using the acquired information.

11. An x-ray detector comprising:
a cathode;
an anode; and
a cadmium tellurium (CdTe) semiconductor detector element disposed between the cathode and the anode, the CdTe semiconductor detector element is configured to convert x-rays emitted from a dual-energy transverse scanning x-ray source into a current that is proportional to the x-ray energy, and the anode comprises at least one of an indium material or an aluminum material and the cathode comprises a platinum material.

12. The x-ray detector in accordance with claim 11 wherein the x-ray detector further comprises a plurality of CdTe semiconductor detector elements arranged to form a linear x-ray detector array.

13. The x-ray detector in accordance with claim 11 wherein the x-ray detector further comprises a plurality of CdTe semiconductor detector elements, each CdTe semiconductor detector element having a photon-counting element.

14. The x-ray detector in accordance with claim 11 wherein the x-ray detector further comprises a plurality of CdTe semiconductor detector elements arranged in a staggered pattern.

15. The x-ray detector in accordance with claim 11 wherein the x-ray detector further comprises a plurality of CdTe semiconductor detector elements and a Schottky contact formed on each semiconductor detector element.

16. The x-ray detector in accordance with claim 11 wherein the anode comprises a Schottky contact.

17. The x-ray detector in accordance with claim 11 wherein the x-ray detector further comprises a plurality of CdTe semiconductor detector elements, and a portion of the CdTe semiconductor detector elements are separated by a gap.

18. A method of fabricating a dual-energy system x-ray detector, said method comprising:
depositing a platinum cathode on a first surface of a cadmium tellurium (CdTe) semiconductor detector element that is configured to convert x-rays emitted from a dual-energy transverse scanning x-ray source into a current that is proportional to the x-ray energy; and
depositing at least one of an indium Schottky contact or an aluminum Schottky contact on an opposite surface of the CdTe semiconductor detector element.

19. A method in accordance with claim 18 further comprising arranging a plurality of CdTe semiconductor detector elements to form at least one each of a linear detector array and a staggered detector array.

20. A scanning bone densitometer comprising:
an x-ray source configured to produce x-rays; and
an x-ray detector configured to receive x-rays emitted from the x-ray source, the x-ray detector including a cadmium tellurium (CdTe) semiconductor detector element, wherein the CdTe semiconductor detector element comprises an anode and a cathode, the anode comprising at least one of an indium material or an aluminum material and the cathode comprising a platinum material.

* * * * *